(12) United States Patent
Schwyn et al.

(10) Patent No.: US 8,016,510 B2
(45) Date of Patent: Sep. 13, 2011

(54) JOINT FOR MOVABLY CONNECTING TWO STABILIZING ELEMENTS

(75) Inventors: Ronald Schwyn, Davos-Glaris (CH); Silvio Koller, Davos (CH); Daniel Schmucki, Stallikon (CH)

(73) Assignee: Synthes USA, LLC, West Chester, PA (US)

( * ) Notice: Subject to any disclaimer, the term of this patent is extended or adjusted under 35 U.S.C. 154(b) by 1796 days.

(21) Appl. No.: 11/150,583

(22) Filed: Jun. 9, 2005

(65) Prior Publication Data

US 2006/0056908 A1  Mar. 16, 2006

Related U.S. Application Data

(63) Continuation of application No. PCT/CH02/00676, filed on Dec. 9, 2002.

(51) Int. Cl.
  *F16C 11/10* (2006.01)

(52) U.S. Cl. .......................... 403/97; 600/102; 606/246

(58) Field of Classification Search .................. 606/103, 606/246, 250, 257, 54–59, 71; 403/61, 81, 403/53, 54, 36, 38, 39, 97; 384/556, 624
See application file for complete search history.

(56) References Cited

U.S. PATENT DOCUMENTS

| | | | | |
|---|---|---|---|---|
| 2,792,813 A * | 5/1957 | Fixman et al. | .................. | 91/217 |
| 3,509,876 A | 5/1970 | Pilz | | |
| 3,638,973 A * | 2/1972 | Poletti | ............................ | 285/184 |
| 3,760,911 A * | 9/1973 | Porter et al. | .................. | 188/300 |
| 4,425,050 A * | 1/1984 | Durand | ............................ | 403/15 |
| 4,431,329 A | 2/1984 | Baitella | | |
| 4,917,343 A * | 4/1990 | Wainscott | .................. | 248/447.2 |
| 5,020,933 A * | 6/1991 | Salvestro et al. | .............. | 403/90 |
| 5,069,320 A * | 12/1991 | Falk | .............. | 192/56.1 |
| 5,123,768 A * | 6/1992 | Franklin | ........................ | 403/96 |
| 5,375,823 A * | 12/1994 | Navas | ........................ | 623/17.15 |
| 5,431,659 A * | 7/1995 | Ross et al. | .................... | 606/103 |
| 5,694,818 A * | 12/1997 | Nickipuck | ........................ | 81/60 |
| 5,765,958 A * | 6/1998 | Lan | .................. | 403/97 |
| 5,824,007 A | 10/1998 | Faraz et al. | | |
| 5,918,844 A * | 7/1999 | Ognier | ........................ | 248/276.1 |
| 6,213,671 B1 | 4/2001 | Chang | | |
| 6,340,354 B1 * | 1/2002 | Rambin | .......................... | 604/22 |
| 6,632,170 B1 * | 10/2003 | Bohanan et al. | .............. | 600/102 |
| 6,742,954 B2 * | 6/2004 | Jouko | .............................. | 403/38 |
| 2001/0024045 A1* | 9/2001 | Bertini | ........................ | 294/119.1 |
| 2001/0029796 A1* | 10/2001 | Magaribuchi | ................ | 74/89.17 |
| 2002/0037119 A1 | 3/2002 | Schleinitz | | |
| 2002/0114703 A1* | 8/2002 | Bodzak | .......................... | 417/62 |
| 2002/0131814 A1* | 9/2002 | Hou et al. | ........................ | 403/97 |

FOREIGN PATENT DOCUMENTS

WO  WO 01/34985 A1  5/2001

* cited by examiner

*Primary Examiner* — Eduardo C Robert
*Assistant Examiner* — Jerry Cumberledge
(74) *Attorney, Agent, or Firm* — Fay Kaplun & Marcin, LLP

(57) ABSTRACT

The invention relates to a joint for movably connecting two stabilizing elements. The joint includes at least two joint segments, which can be rotated relative to each other. Each joint segment is connected to a respective stabilizing element. The joint can be releasably locked by locking means, and the locking means can be locked and/or unlocked by a fluid that is supplied and/or discharged via conduits.

12 Claims, 4 Drawing Sheets

JOINT FOR MOVABLY CONNECTING TWO STABILIZING ELEMENTS

CROSS REFERENCE TO RELATED APPLICATION

This is a continuation of, and claims priority under 35 U.S.C. §120 to International Patent Application No. PCT/CH2002/000676, filed Dec. 9, 2002, the entire contents of which are incorporated herein by reference thereto.

TECHNICAL FIELD OF THE INVENTION

The invention relates to a joint for movably connecting two stabilizing elements to each other and/or to a holding arm that can be used for surgical purposes and/or to a holding device for bones, particularly bone fragments.

BACKGROUND OF THE INVENTION

The correct alignment of bone fragments is an important surgical step in osteosynthesis. In repositioning bone fragments, and in particular, for example, long bones, the pelvis, or bone joints, relatively large forces may act on the bone fragments, so that a holding device for bone fragments can be very advantageous for the surgeon. Using such a device, one of the main bone fragments can be held in place after it has been at least approximately aligned, so that its position remains constant, particularly during long procedures.

A holding device for use during surgical procedures is known. This known device comprises two stabilizing elements that can be pivoted relative to one another. Each element has a joint at its end, in addition to a joint between the stabilizing elements. All three joints can be locked in place by locking means, which can be activated by means of a single operating instrument. The functioning of the locking means as well as their activation is purely mechanical. The joint, disposed between the relatively long stabilizing elements, is locked by a friction lock via the manual tightening of a screw connection. A disadvantage of this known holding device is that it is restricted to relatively small locking forces and therefore to relatively short stabilizing elements.

SUMMARY OF THE INVENTION

The invention is directed to a releasably lockable joint between two stabilizing elements of a holding device. The invention advantageously permits stable locking of the joint between the stabilizing elements even when large forces act on the stabilizing elements.

The invention is also directed to a holding arm for surgical purposes and to a holding device for bone fragments.

One of the advantageous features of the invention includes a fluid-driven locking means that allows a high locking force to be exerted on the joint. Thus, when high torques are exerted on the joint, the stabilizing elements of a holding arm can be held in an exact position, and precise positioning of a bone or bone fragment attached to a stabilizing element, for example, is possible even during a lengthy repositioning procedure.

The fluid for locking the joint or joints is preferably compressed air. Instead of compressed air, the locking means can also be operated by means of a vacuum.

In a preferred embodiment, the inventive joint has only a single axis of rotation. In comparison with ball joints having several axes of rotation, this embodiment enables the releasably lockable joint to be configured in a simple manner, for example, by means of a single pneumatic cylinder.

In another embodiment, a first joint segment of the joint has a cavity coaxial to the axis of rotation, while the locking means comprises a piston that is displaceable in the cavity, parallel to the axis of rotation. The piston can be pressed against a second joint segment by means of supplying and/or discharging the fluid. In this manner, a pneumatic cylinder operated with compressed air, for example, can be integrated into the joint parts, thereby making it possible to achieve a compact construction of the joint. The piston is preferably guided by a coaxial axle and at least one second axle disposed eccentrically in the cavity, whereby both axles are secured to the first joint segment. In this way, an exact coaxial displaceability of the piston is ensured, while a rotation of the piston relative to the first joint segment is prevented by the eccentric axle.

Preferably, the piston has a front face that stands crosswise to the axis of rotation and that can be pressed against the second joint segment. The piston also has a rear face that stands crosswise to the axis of rotation. If the fluid has pressure applied to it, the fluid is preferably guided into the cavity delimited and sealed by the rear face of the piston via one or more supply/discharge lines. In an embodiment in which the locking means is operated by means of a vacuum, a cavity between the front face of the piston and the second joint segment, for example, can be evacuated.

In another embodiment, the contact surface of the second joint segment, which stands crosswise to the axis of rotation and is directed against the first joint segment, and the front face of the piston are provided with toothed gear wheels that can be brought into engagement with one another. By means of these toothed gear wheels, which can be brought into a positive-lock engagement, the holding force that prevents a relative rotation of the two joint segments about the axis of rotation in the locked state can be significantly increased. The toothed gear wheels are structured in such a manner that the joint can be locked in steps, at a specific angle of rotation. The size of the steps is dependent on the size of the joint.

In another embodiment of the invention, the toothed gear wheels are structured such that the joint can be locked in 2° steps of angular rotation.

In yet another embodiment, the second joint segment comprises elastic deformable means that can be elastically compressed parallel to the axis of rotation in response to a displacement of the piston against the second joint segment. Preferably, the elastic means are structured as pressure springs that are disposed between the second joint segment and the piston. In this way, locking of the joint by means of the locking means is merely performed by means of a fluid to which pressure or vacuum is applied, while unlocking takes place by means of the spring force of the elastic deformable means.

In another embodiment, the second joint segment comprises a cavity (referred to herein as the "second cavity") that can be delimited relative to the first joint segment by the piston, instead of the elastically deformable means. A fluid to which pressure is applied can be supplied to the second cavity by way of a second line. In this embodiment, the locking means act as dual-action cylinders, such as, for example, compressed air cylinders.

Preferably, at least one connection element for the lines is affixed to the housing of the first joint segment, so that fluid to be supplied and/or discharged in the lines can be supplied to or discharged from the cavity of the first joint segment by means of these connection elements.

In a preferred embodiment of a holding arm, the arm comprises at least two stabilizing elements disposed between the two ends of the holding arm. The two stabilizing elements are movably connected to one another by a joint of the invention. Each of the two stabilizing elements connected to the joint is connected to a respective joint segment of the joint.

The holding device serves to fix bones or bone fragments of a patient positioned on an object, such as, for example, an operating table or operating chair, that is preferably fixed in place relative to the patient. Positioning of the holding device on the ceiling of the operating room, or a free-standing set-up of the holding device on the floor of the operating room, or leaning against another object, is also possible. The holding device comprises a movable holding arm having a first end and a second end, whereby at least one first and one second stabilizing element, connected by means of a joint, are disposed on the holding arm between the first and the second ends. Attachment means for fixing the holding arm in place on an object fixed in place relative to the patient, for example the operating table, are disposed on the first end of the holding arm, while fixation means for releasable fixation of a bone or bone fragment of a patient are disposed on the second end of the holding arm.

In a preferred embodiment of a holding device, the device comprises at least two, preferably three joints. The axes of rotation of the individual joints can run parallel, or be disposed at a slant, preferably perpendicular to one another, so that in the case of an embodiment having three joints, the second end of the holding arm can be moved in space relative to three coordinate axes that stand perpendicular to one another.

In another embodiment of a holding device, the device comprises three stabilizing elements and four joints, whereby one joint is disposed between each of two stabilizing elements, one joint between the one end-position stabilizing element and the attachment means, and another joint between the second end-position stabilizing element and the fixation means. This embodiment permits a movement of the holding arm relative to the operating table, while the fixation means can be aligned relative to the holding arm. Therefore the holding arm can be positioned by the surgeon when the joints are unlocked, and locked in the desired position by means of a single switch, for example a foot switch, after the second end has been fixed in place on the bone or bone fragment to be held in place by means of the fixation means.

Instead of simultaneous locking of all the joints disposed on the holding arm by means of activating a single switch, the control and/or the lines for supply or discharge of the fluid can be laid out such that the joints can be individually locked by means of activating one or more switches.

In addition to Kirschner wires, the following can be alternatively used as fixation means: bone clamps, Schanz screws, plates, or endomedullar hooks or nails.

The attachment means for fixing the holding arm in place on, for example, an operating table, can comprise one or more clamping jaws. Because of the weight of the holding arm, a carrier is preferably passed through below the operating table, between two side edges of the operating table, so that attachment takes place on both sides of the operating table, making it possible to better absorb the forces and torques that occur due to the weight of the holding arm. The weight of the holding arm can then be compensated by means of a gas pressure spring, for example.

BRIEF DESCRIPTION OF THE DRAWINGS

The detailed description will be better understood in conjunction with the accompanying drawings, in which like reference characters represent like elements, as follows.

DETAILED DESCRIPTION OF THE INVENTION

Figure 1:
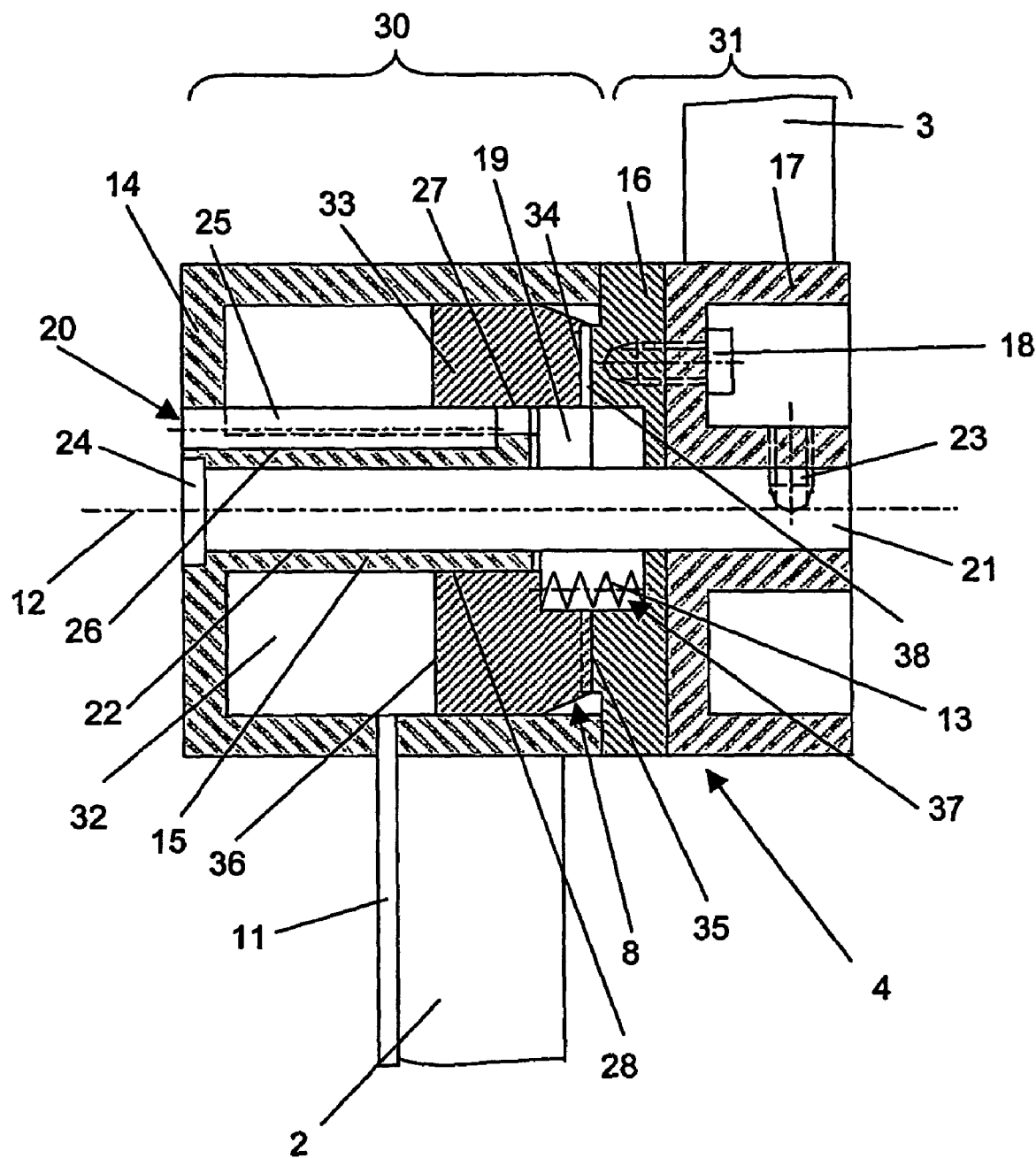
FIG. 1 shows a section through an embodiment of a joint of the invention.

FIG. 1 shows an embodiment of a joint 4, preferably operated with compressed air and having only a single axis of rotation between two stabilizing elements 2, 3. Joint 4 comprises two joint segments 30, 31 that can rotate relative to one another about an axis of rotation 12. Each joint segment is connected to a respective one of the stabilizing elements 2, 3. Joint segments 30, 31 are held together axially by means of a bolt 21, which is coaxial to axis of rotation 12. Bolt 21 is accommodated in a bore 22 that passes coaxially through the two joint segments 30, 31. Bolt 21 has a head 24 that is enlarged in diameter at an end of bolt 21, accommodated in first joint segment 30. A screw 23 that can be screwed in perpendicular to the axis of rotation 12 is disposed in the second joint segment 31, by means of which bolt 21 is secured in bore 22 axially and rotationally, when joint segments 30, 31 rest against one another. Joint 4 can be locked and unlocked by locking means 8. Locking means 8 can have compressed air applied to it by way of a supply/discharge line 11, where in one embodiment, locking means 8 can be locked by supplying compressed air, and unlocked by discharging compressed air. The first joint segment 30 includes a housing 14 having a hollow-cylinder journal 15 concentric to the axis of rotation 12. First joint segment 30 also has a cavity 32 coaxial to the axis of rotation 12. Here, locking means 8 for locking joint 4 includes a piston 33 that is displaceable in cavity 32, parallel to the axis of rotation 12, which can be pressed against the second joint segment 31 by means of supplying or discharging compressed air. Piston 33 comprises a front face 35 that stands crosswise to the axis of rotation 12 and can be pressed against the second joint segment 31. Piston 33 also comprises a rear face 36 that stands crosswise to the axis of rotation 12. The compressed air can be supplied to cavity 32 delimited by a second face 36 of the piston 33 by way of line 11. Piston 33 is also structured as a hollow cylinder and mounted on journal 15, displaceable parallel to the axis of rotation 12. Here, the second joint segment 31 includes two parts 16, 17 disposed axially one behind the other and rigidly connected with one another by means of four screws 18. The first part 16 of the second joint segment 31 has a contact surface 34 that stands crosswise to the axis of rotation 12, directed against the first joint segment 30. This contact surface 34 as well as the front face 35 of piston 33 are provided with ring-shaped toothed gear wheels 38 that can be brought into engagement with one another and are concentric to the axis of rotation 12. The ring-shaped toothed gear wheels 38 form the periphery of a second coaxial cavity 19, which penetrates into the first part 16 of the second joint segment 31 from the contact surface 34, on the one hand, and penetrates into the piston 33 from the front face 35, on the other hand. The elastically deformable means 37, which are configured as pressure spring 13, are disposed in the second cavity 19. The three pressure springs 13 are uniformly distributed on the circumference and have ends that rest against the first part 16 of the second joint segment 31 and on the piston 33. These pressure springs 13 are elastically compressed, parallel to the axis of rotation 12, in the case of a displacement of the piston 33 against the second joint segment 31, so that in the case of a discharge of the compressed air in the cavity 32, the piston 33 is pushed back into its starting position when joint 4 is unlocked, by means of the recovery force of the pressure springs 13. Piston 33 is secured against rotation about the axis of rotation 12 by means of a rotation-securing device 20, in the first joint segment 30. Here, this rotation-securing device 20 comprises a cylindrical rod 25 that is accommodated, eccentrically with reference to the axis of rotation 12, in a notch 26 recessed into the periphery of the journal 15, on the one hand, and in a groove 27 made in the bore 28 in the piston 33, on the other hand. Furthermore, the cylindrical rod 25 is attached in the housing 14 at one of its ends.

Figure 4:
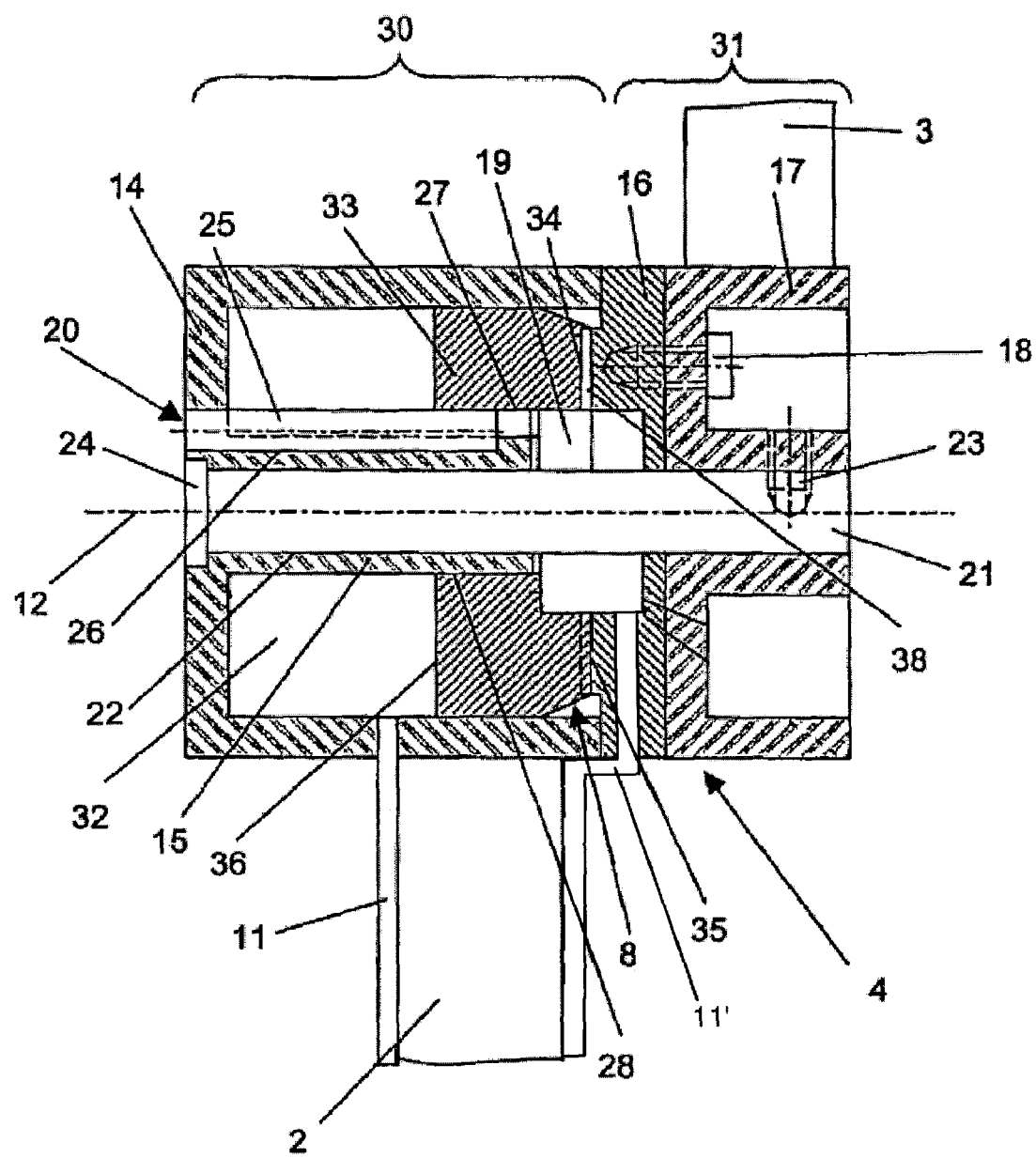
FIG. 4 shows a cross-sectional view of a joint according to an alternate embodiment of the present invention.

In an alternative embodiment, as shown in FIG. 4, rather than including the elastically deformable means 37, the second cavity 19 of the second joint segment 31 may be delimited relative to the first joint segment 30 by the piston 33. A fluid to which pressure is applied can be supplied to the second cavity 19 by way of a second line 11' for supplying and/or discharging fluids. In this embodiment, the locking means 8 acts via dual-action cylinders such as, for example, compressed air cylinders.

Figure 2:
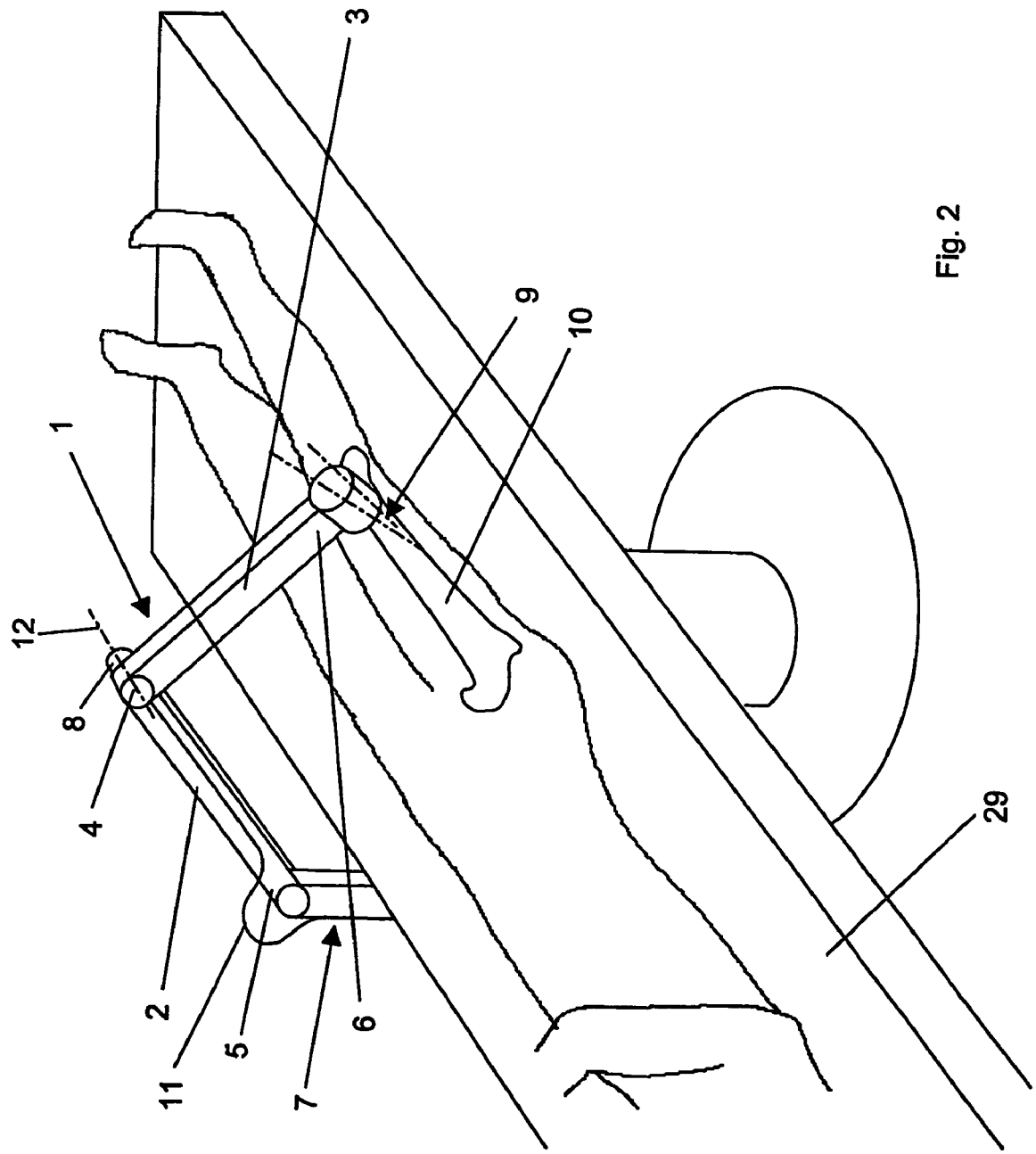
FIG. 2 shows a perspective view of an embodiment of a holding device of the invention.

FIG. 2 shows an embodiment of the inventive holding device, having a holding arm 1 comprising a first stabilizing element 2 and a second stabilizing element 3. The holding device essentially comprises a movable holding arm 1 having a first end 5 and a second end 6. The stabilizing elements 2, 3 are disposed between the two ends 5, 6, and are connected with one another by means of a joint 4, so as to rotate about the axis of rotation 12. Furthermore, the holding device comprises attachment means 7 at the first end 5 of the holding arm 1, which means are structured here as a rod that is attached to the operating table 29, and serve to fix the holding arm 1 in place on the operating table 29. Here, attachment means 7 are connected to the first stabilizing element 2 so as to rotate. Fixation means 9, such as, for example, Kirschner wires for releasable fixation of free end 6 to a bone 10 of a bone fragment of a patient, are disposed on the second end 6 of the holding arm 1.

Figure 3:
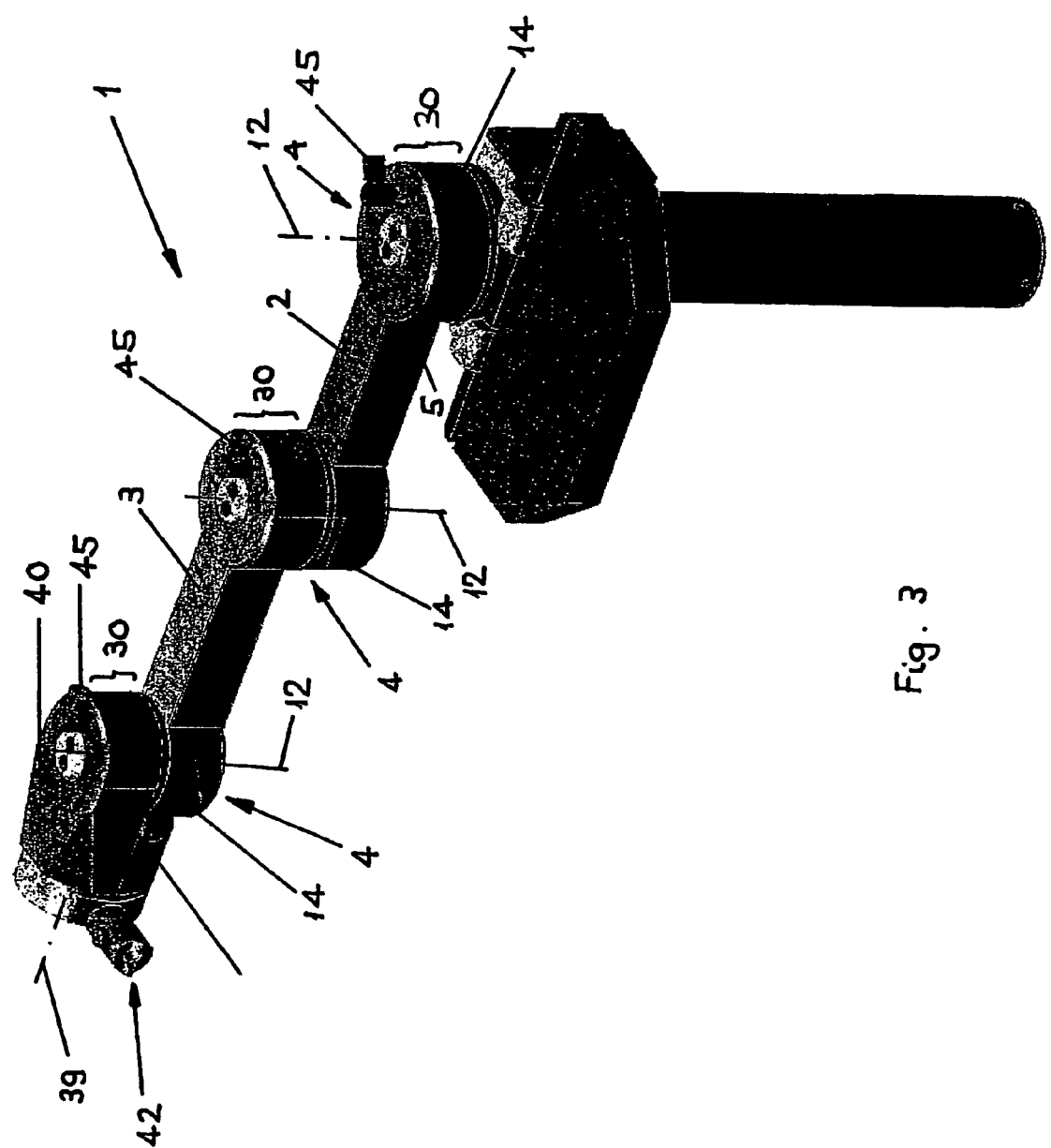
FIG. 3 shows a perspective view of an embodiment of a holding device of the invention, having three joints.

FIG. 3 shows an embodiment of the inventive holding device, having three stabilizing elements 2,3,40, of which two stabilizing elements 2,3,40, in each instance, are connected with one another by a joint 4, in each instance. The stabilizing element 2 that is in the end position on the first end 5 of the holding arm 1 is attached to a fixed object 41, by means of another joint 4, with the attachment means 7 configured as a clamp. Here, the axes of rotation 12 of the three joints 4 are parallel. Furthermore, the accommodations 42 for the fixation means 9 (FIG. 2) are connected with the end-position stabilizing element 40 on the second end 6 of the holding arm 1, to rotate about a second axis of rotation 39 that stands perpendicular to the axes of rotation 12. Connection elements 45 are affixed to the housings 14 of the joint segments 30, to which the lines 11 and 11' (FIGS. 1, can be connected. In this connection, the lines 11 and 11' can be run in series or parallel, as needed. The control for the compressed air feed can, on the one hand, be configured such that joints 4 can be locked individually, in any desired sequence, or one after the other, or, on the other hand, in such a manner that the joints 4 can be locked simultaneously.

While it is apparent that the illustrative embodiments of the invention disclosed herein fulfill the objectives stated above, it will be appreciated that numerous modifications and other embodiments may be devised by those skilled in the art. Various features and structures can be used singularly or in combination with other features and structures. Therefore, it will be understood that the appended claims are intended to cover all such modifications and embodiments which come within the spirit and scope of the invention.

We claim:
1. A joint movably connecting two stabilizing elements, the joint comprising:
    first and second segments that can rotate relative to each other about an axis of rotation, each joint segment connected to a respective stabilizing element extending radially outward from the axis of rotation, the respective stabilizing elements pivoting relative to one another, the first joint segment having a cavity coaxial to the axis of rotation;
    locking means for releasably locking the joint, the locking means comprising a piston displaceable in the cavity and parallel to the axis of rotation;
    a line one of supplying and discharging a fluid in communication with the locking means wherein the locking means can be locked by the fluid being supplied and unlocked by the fluid being discharged via the line; wherein:
    the piston can be pressed against the second joint segment by means of supplying or discharging fluid;
    the piston comprises a front face that stands crosswise to the axis of rotation, the front face operative to be pressed against the second joint segment;
    the piston also comprises a rear face that stands crosswise to the axis of rotation;
    the fluid can have pressure applied to it and can be supplied to the cavity delimited by the rear face of the piston via the line; and
    the second joint segment comprises a contact surface that stands crosswise to the axis of rotation and is directed against the first joint segment, the contact surface and the front face of the piston comprising toothed gear wheels that can be brought into engagement with one another.

2. The joint of claim 1 wherein the first and second joint segments can be rotated relative to one another about only the axis of rotation.

3. The joint of claim 1 wherein the second joint segment comprises elastic deformable means that can be elastically compressed parallel to the axis of rotation in response to a displacement of the piston against the second joint segment.

4. The joint of claim 1 wherein:
    the second joint segment has a cavity that can be delimited relative to the first joint segment by means of the piston; and
    the joint further comprises a second line in communication with the cavity of the second joint segment to supply the cavity with a fluid to which pressure can be applied, the second line one of supplying and discharging the fluid to which the pressure is applied.

5. The joint of claim 4 wherein the first joint segment has a housing that comprises a least one connection element for the second line to supply or discharge fluid to or from the second joint segment cavity.

6. The joint of claim 1 further comprising a rotation-securing device secured to the piston in the first joint segment to prevent rotation about the axis of rotation.

7. The joint of claim 1 wherein the stabilizing elements are rod-shaped and connected to one of the joint segments at least at an end of an element.

8. The joint of claim 1 further comprising a further joint and a further stabilizing element, wherein the further joint is disposed between the stabilizing element connected to the second segment and the further stabilizing element.

9. The joint of claim 8 wherein the stabilizing element connected to the first segment couples to an attachment device operative to secure the joint to an object, and the further stabilizing element couples to a bone fixation device.

10. The joint of claim 9 wherein the object is one of an operating table and an operating chair.

11. The joint of claim 8 wherein the axis of rotation and an axis of rotation of the further joint are nonparallel to one another.

12. The joint of claim 8 wherein the axis of rotation and an axis of rotation of the further joint run parallel to one another.

* * * * *